US012023525B1

United States Patent
Kang

(10) Patent No.: US 12,023,525 B1
(45) Date of Patent: Jul. 2, 2024

(54) FOCUSED ULTRASOUND FOR RELIEVING PAIN AND SWELLING IN SKIN TREATMENT USING ELECTRIC MUSCLE STIMULATION AND COOLING

(71) Applicant: SHENB Co., Ltd., Seoul (KR)

(72) Inventor: Sun Young Kang, Seoul (KR)

(73) Assignee: SHENB Co., Ltd., Seoul (KR)

( * ) Notice: Subject to any disclaimer, the term of this patent is extended or adjusted under 35 U.S.C. 154(b) by 0 days.

(21) Appl. No.: 18/532,371

(22) Filed: Dec. 7, 2023

(30) Foreign Application Priority Data

Dec. 8, 2022 (KR) .................. 10-2022-0170872

(51) Int. Cl.
*A61N 7/02* (2006.01)
*A61F 7/00* (2006.01)
*A61N 1/36* (2006.01)
*H10N 10/13* (2023.01)

(52) U.S. Cl.
CPC ............... *A61N 7/02* (2013.01); *A61F 7/007* (2013.01); *A61N 1/36014* (2013.01); *H10N 10/13* (2023.02); *A61F 2007/0075* (2013.01); *A61F 2007/0087* (2013.01)

(58) Field of Classification Search
CPC ....... A61N 7/02; A61N 1/36014; A61F 7/007; A61F 2007/0075; A61F 2007/0087; H10N 10/13
See application file for complete search history.

(56) References Cited

FOREIGN PATENT DOCUMENTS

| KR | 10-2020-0000754 A | 1/2020 |
|----|-------------------|--------|
| KR | 10-2020-0006861 A | 1/2020 |
| KR | 10-2022-0000119 A | 1/2022 |
| KR | 20-2022-0000119 U | 1/2022 |
| KR | 10-2551710 B1 | 7/2023 |

OTHER PUBLICATIONS

Korean Office Action dated Jun. 12, 2023 in corresponding Korean Patent Application No. 10-2022-0170872. (5 pages in English and 5 pages in Korean).
Korean Office Action dated Feb. 9, 2023 in corresponding Korean Patent Application No. 10-2022-0170872. (5 pages in English and 5 pages in Korean.
International Search Report No. PCT/KR2023/018825 issued on Mar. 4, 2024 (4 Pages in English).

*Primary Examiner* — Serkan Akar
(74) *Attorney, Agent, or Firm* — NSIP Law

(57) ABSTRACT

The present disclosure relates to a handpiece for relieving pain and swelling in skin of a person being treated, including a housing, a cartridge having a transducer that emits ultrasonic waves, and a vertical movement unit mounted in the housing and configured to move the transducer in a vertical direction by a magnetic force.

4 Claims, 6 Drawing Sheets

FOCUSED ULTRASOUND FOR RELIEVING PAIN AND SWELLING IN SKIN TREATMENT USING ELECTRIC MUSCLE STIMULATION AND COOLING

CROSS-REFERENCE TO RELATED APPLICATIONS

This application claims priority to Korean Patent Application No. 10-2022-0170872, filed on Dec. 8, 2022, the entire contents of which are incorporated herein by reference.

Technical Field

The present disclosure relates to a handpiece capable of focusing ultrasonic waves under the skin of a person being treated, and, more specifically, to a handpiece capable of relieving pain and swelling in the skin of a person being treated.

BACKGROUND

High-intensity focused ultrasound energy refers to energy collected by focusing ultrasonic waves on a specific point.

Treatment using such high-intensity focused ultrasound energy is based on a thermal effect in which heat is generated when ultrasound waves are focused on a certain point, causing the temperature to rise rapidly.

Heat generated by high-intensity focused ultrasound energy burns and removes specific subcutaneous tissue such as an intradermal tumor, or may cause degeneration and regeneration of subcutaneous tissue so as to be used for skin care or plastic surgery for erasing wrinkles, etc.

In particular, when heat is delivered to the skin, while skin tissue is recovering from heat, the components of the skin such as collagen and elastin are reactivated and the elasticity of the loose skin tissue increases.

For example, in the case of an eyebrow lifting treatment using high-intensity focused ultrasonic waves, when high-intensity focused ultrasound energy stimulates the fascial layer, the spiral muscle fibers become more twisted, thereby strengthening the fascia and improving the sagging skin.

A handpiece that generates high-intensity focused ultrasonic energy includes a handpiece case and a cartridge that is mounted in the handpiece case and contains a transducer that generates ultrasonic waves.

However, in conventional handpieces, since a cartridge is fixed at a specific point inside a handpiece case, there is a problem that the cartridge has to be replaced with a new cartridge with a transducer that has a different focal length in order to adjust the depth at which ultrasonic waves are focused under the skin.

Meanwhile, treatment using high-intensity focused ultrasound energy increases the temperature of subcutaneous tissue, which causes a person being treated to feel pain or swelling in the person's skin. Recently, there has been an increasing interest in handpieces capable of appropriately and effectively managing such pain and swelling.

PRIOR ART DOCUMENTS

Patent Documents

Patent Document 1: Korean Laid-open Patent Publication No. 10-2020-0006861 (Jan. 21, 2020)

SUMMARY

The present disclosure has been made in an effort to resolve the above-mentioned problems by providing a handpiece capable of moving a transducer in a vertical direction and appropriately relieving pain and swelling in the skin of a person being treated.

The handpiece for relieving pain and swelling in the skin of a person being treated according to the present disclosure may include a housing, a cartridge having a transducer that emits ultrasonic waves, and a vertical movement unit mounted in the housing and configured to move the transducer in a vertical direction by a magnetic force.

The vertical movement unit may include a magnet disposed in the housing and a magnetic body fixed to the transducer. The magnetic body may be configured to move the transducer in a vertical direction while a distance between the magnet and the magnetic body is adjusted by the magnetic force.

The vertical movement unit may further include an elastic unit for separating the magnet and the magnetic body from each other.

The magnet may be an electromagnet.

The cartridge may include a skin cooling unit for cooling the skin of a person being treated and an electrical muscle stimulation (EMS) skin stimulation unit positioned adjacent to the skin cooling unit and providing an electrical stimulation to the skin of the person being treated.

The skin cooling unit may include a cooling plate and a thermoelectric element. An opening through which ultrasonic waves generated by the transducer pass may be formed at a lower part of the cooling plate, and the cooling plate may be in contact with the skin of the person to absorb heat from the skin of the person being treated. The thermoelectric element may absorb heat from the cooling plate to cool the cooling plate.

The EMS skin stimulation unit may include an EMS pad for providing an electrical stimulation for relieving pain in the skin of the person being treated and an EMS control module for controlling a current delivered to the skin of the person being treated by the EMS pad.

The handpiece for relieving pain in and swelling of the skin of a person being treated according to the present disclosure may be capable of quickly moving a transducer, thereby preventing ultrasonic waves from being focused on unwanted subcutaneous points, and appropriately relieving pain in and swelling of the skin of a person being treated.

DETAILED DESCRIPTION

Figure 1:
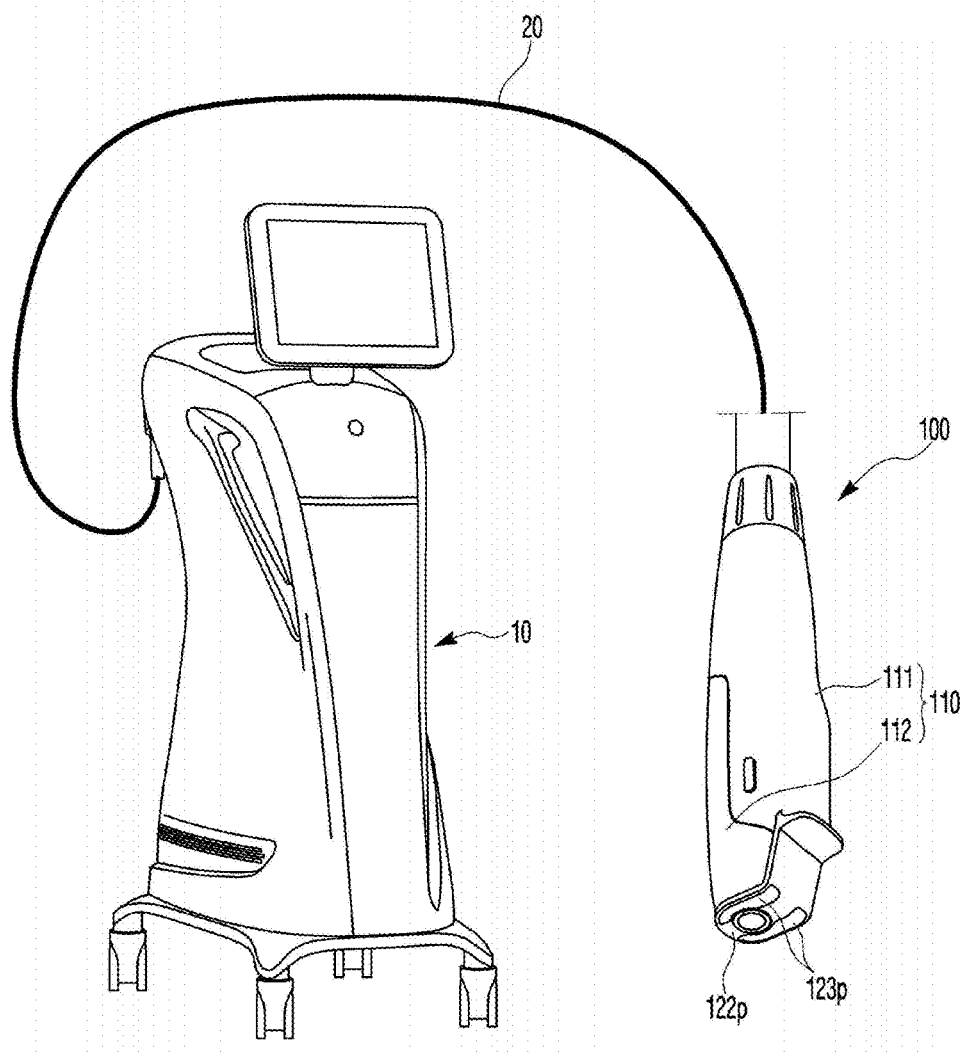
FIG. 1 is a perspective view of a handpiece capable of relieving pain and swelling in the skin of a person being treated according to an embodiment of the present disclosure, which is connected to a main controller.

Hereinafter, some embodiments of the present disclosure will be described in detail with reference to the illustrative drawings. It should be noted that, when assigning reference numerals to components in each drawing, identical components have been given the same reference numerals as much as possible even when they are shown in different drawings.

In addition, in describing the embodiments of the present disclosure, when it is determined that detailed descriptions of related known features or functions impede understanding of the embodiments of the present disclosure, the detailed descriptions will not be provided.

Furthermore, to describe certain components in the embodiments of the present disclosure, terms such as first, second, A, B, (a), and (b) may be used. These terms are only used to distinguish the components from other components, and the nature, the sequence, the order, etc. of the components are not limited by the terms.

Figure 2:
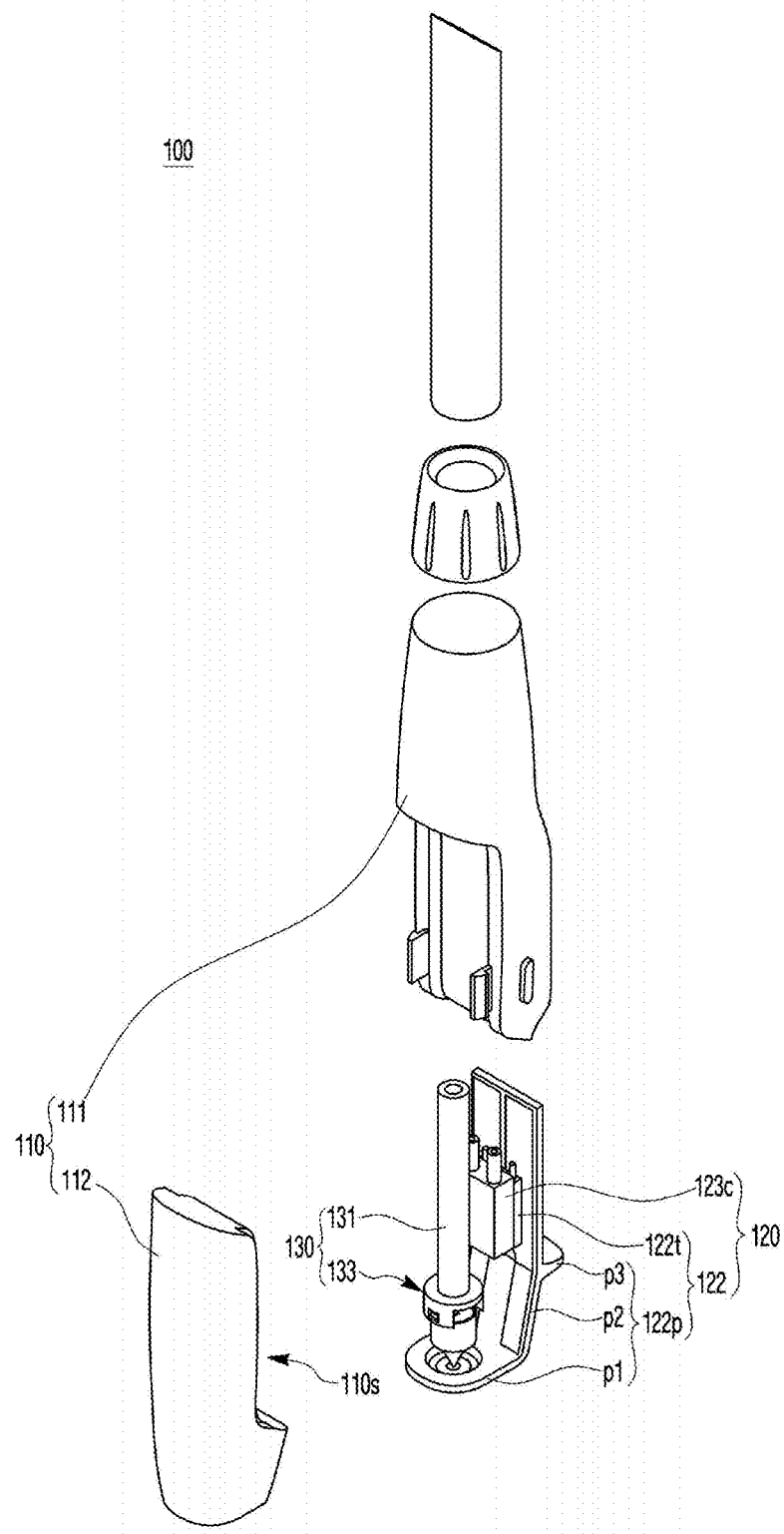
FIGS. 2 and 3 are views for illustrating components in the handpiece in FIG. 1.
Figure 3:
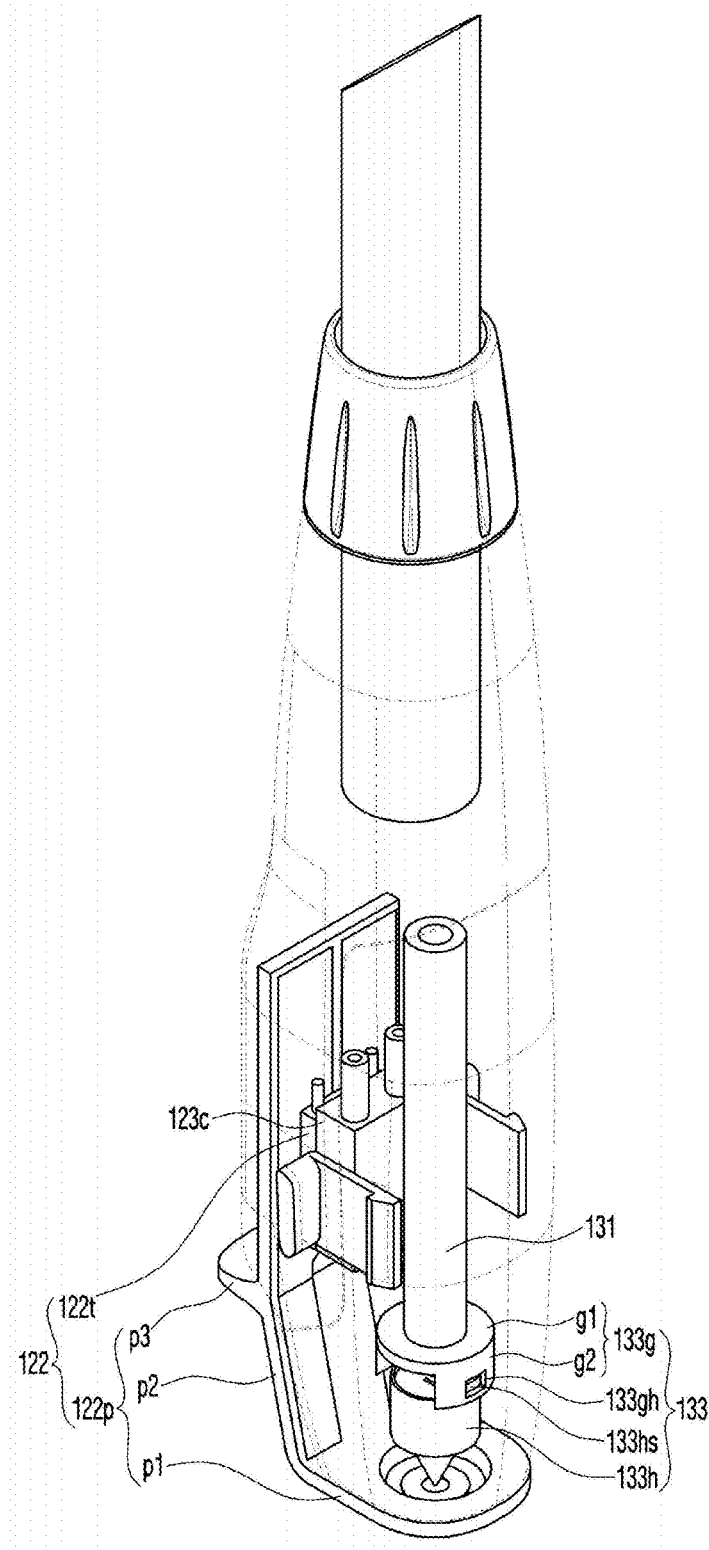
Figure 4:
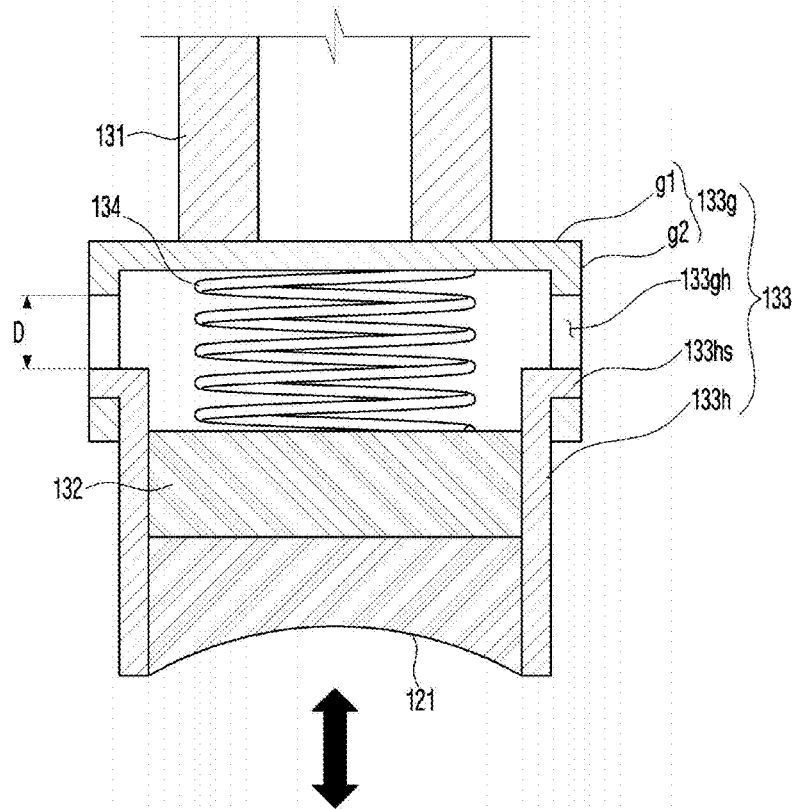
FIG. 4 is a cross-sectional view of a vertical movement unit of the handpiece in FIG. 1.
Figure 5:
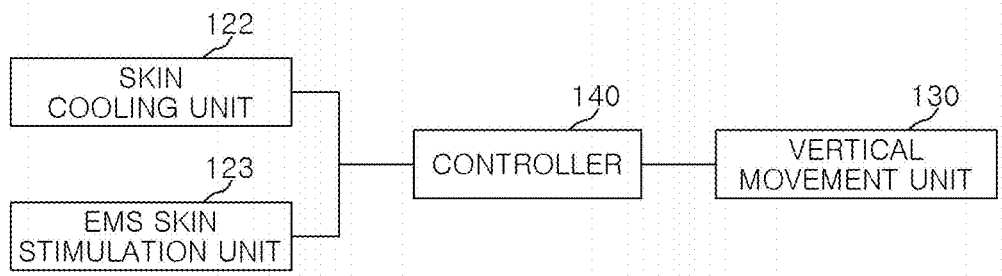
FIG. 5 is a block diagram of a portion of the handpiece in FIG. 1.
Figure 6:
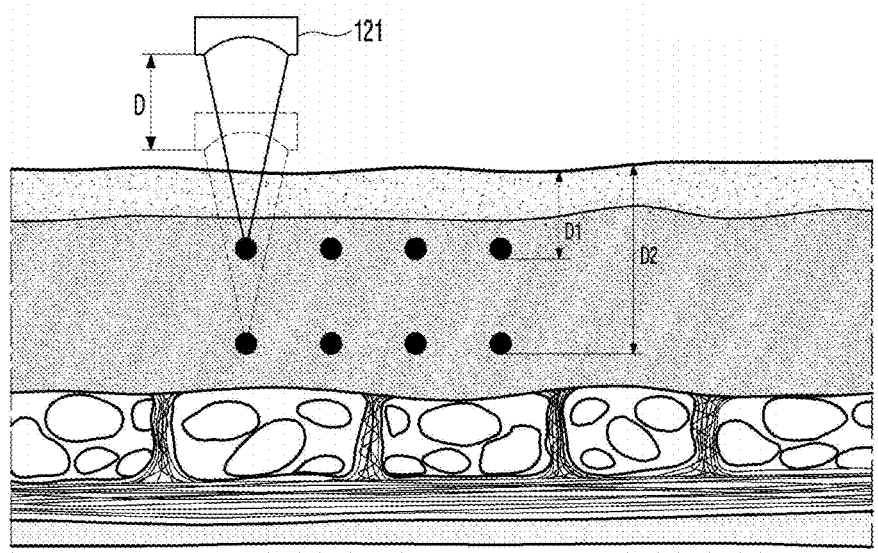
FIG. 6 is a view for illustrating an operation of the handpiece in FIG. 1.
Figure 7A:
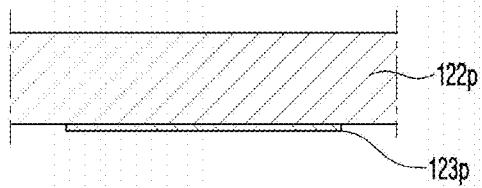
FIGS. 7A to 7C are views for illustrating how an EMS pad and a cooling plate are combined to each other.
Figure 7B:
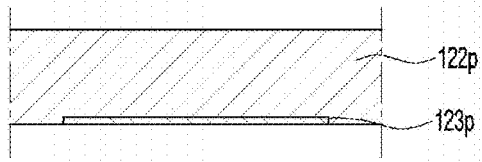
Figure 7C:
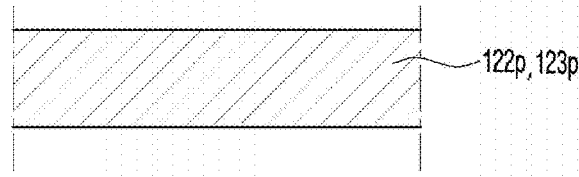

FIG. 1 is a perspective view of a handpiece capable of relieving pain and swelling in the skin of a person being treated according to an embodiment of the present disclosure, which is connected to a main controller. FIGS. 2 and 3 are views for illustrating components in the handpiece in FIG. 1. FIG. 4 is a cross-sectional view of a vertical movement unit of the handpiece in FIG. 1. FIG. 5 is a block diagram of a portion of the handpiece in FIG. 1. FIG. 6 is a view for illustrating the operation of the handpiece in FIG. 1. FIGS. 7A to 7C are views for illustrating how an EMS pad and a cooling plate are combined to each other.

Referring to FIGS. 1 to 6, a handpiece 100 for relieving pain and swelling in the skin of a person being treated according to the present disclosure may be connected to a main controller 10 through a cable 20.

The main controller 10 may include a display, a CPU, a power unit, etc. and provide power and control signals to the handpiece 100 for relieving pain and swelling in the person's skin.

The handpiece 100 for relieving pain and swelling in the person's skin may be operated by the power and the control signals, etc. provided by the main controller 10.

Specifically, the handpiece 100 for relieving pain and swelling in the person's skin may focus ultrasonic waves subcutaneously and generate heat to burn and remove specific subcutaneous tissue such as an intradermal tumor, or may cause degeneration and regeneration of subcutaneous tissue so as to be used for skin care or plastic surgery for erasing wrinkles, etc.

The handpiece 100 for relieving pain and swelling in the person's skin may include a housing 110, a cartridge 120, and a vertical movement unit 130.

A mounting portion 110s may be formed inside the housing 110, and the cartridge 120 may be mounted on the lower part of the housing 110 to be inserted into the mounting portion 110s.

The housing 110 may include a first case 111 and a second case 112.

Electrical components connected to the cable 20 are mounted in the first case 111, and the vertical movement unit 130 may be positioned in the side of the second case 112.

The second case 112 may be detachably mounted on the first case 111, and form the mounting portion 110s.

The cartridge 120 may include a transducer 121, a skin cooling unit 122, and an electrical muscle stimulation (EMS) skin stimulation unit 123.

The transducer 121 may be placed over a lower plate p1 of the skin cooling unit 122 and generate ultrasonic waves.

The transducer 121 may irradiate ultrasonic waves in one shot or continuously.

The skin cooling unit 122 may be exposed to the outside of the housing 110, and may be in contact with the skin of a person being treated during treatment and quickly absorb heat from the skin of the person, thereby alleviating pain in the skin of the person.

Specifically, when the transducer 121 emits ultrasonic waves, the skin cooling unit 122 may come into contact with the skin of a person being treated and quickly absorb heat from the skin of the person.

The skin cooling unit 122 may include a cooling plate 122p and a thermoelectric element 122t.

The cooling plate 122p may include the lower plate p1 and a side plate p2.

An opening through which ultrasonic waves generated by the transducer 121 pass may be formed on the lower plate p1.

In addition, the lower plate p1 may be in contact with the skin of a person being treated and quickly absorb heat from the skin of the person being treated.

The side plate p2 may be connected to one end of the lower plate p1 to form a side surface of the cooling plate 122p.

The thermoelectric element 122t may be installed inside the side plate p2.

The thermoelectric element 122t may be connected to the side plate p2 of the cooling plate 122p to absorb heat from the side plate p2 and cool the entire cooling plate 122p.

For example, the thermoelectric element 122t may include a Peltier module made of $Bi_2TeO_3$, and may convert heat energy absorbed from the cooling plate 122p into electrical energy.

The thermoelectric element 122t may cool the cooling plate 122p to a temperature of 0° C. to 15° C. The cooling plate 122p may absorb heat from the skin heated by focused ultrasonic waves emitted from the transducer 121, thereby relieving pain in the skin of a person being treated.

According to the present disclosure, the side plate p2 may increase the total heat capacity of the cooling plate 122p, thereby minimizing an increase in temperature of the lower plate p1 in contact with the skin of a person being treated.

The cooling plate 122p may further include a protruding plate p3.

An operator may easily attach the cartridge 120 to the lower part of the housing 110 or detach the cartridge 120 therefrom, by pushing or pulling the protruding plate p3 with his or her finger.

In addition, since the protruding plate p3 is a part that increases the weight of the cooling plate 122p, it may also increase the total heat capacity of the cooling plate 122p.

The EMS skin stimulation unit 123 may stimulate the skin of a person being treated by sending a microcurrent to the skin of the person, thereby reducing pain in the skin of the person.

Cooling of the skin of a person being treated by the skin cooling unit 122 and stimulating of the person's skin by the EMS skin stimulation unit 123 may proceed independently or simultaneously.

The EMS skin stimulation unit 123 may include an EMS pad 123p and an EMS control module 123c.

The EMS control module 123c may control the current transmitted to the skin by the EMS pad 123p. Accordingly, the EMS pad 123p may provide electrical stimulation for relieving pain in the skin of a person being treated.

The area of the EMS pad 123p may be less than the area of the cooling plate 122p, and the EMS pad 123p may be formed to be attached to a predetermined portion of the cooling plate 122p.

The EMS pad 123p may be attached to the cooling plate 122p in the form of a film (FIG. 7A). Alternatively, the EMS pad 123p may be attached into a groove that is formed in the cooling plate 122p with a thickness less than or equal to the thickness of the EMS pad 123p (FIG. 7B).

Alternatively, the cooling plate 122p and the EMS pad 123p may be formed integrally (FIG. 7C). In this case, the cooling plate 122p and the EMS pad 123p may be formed as one plate, and cooling of the skin and electrically stimulating of the skin may proceed independently or simultaneously.

The EMS control module 123c may control the EMS pad 123p to apply a microcurrent with an intensity of 1 mA to 100 mA and a frequency of 0 kHz to 10 kHz to the skin of a person.

The vertical movement unit 130 may be mounted inside the housing 110 and move the transducer 121 in a vertical direction.

Specifically, the vertical movement unit 130 may be arranged in the second case 112.

For example, the vertical movement unit 130 may move the transducer 121 in a vertical direction by a predetermined distance D in the range from 1.5 mm to 4.5 mm, and may adjust the depth D1 and D2 at which ultrasonic waves generated by the transducer 121 are focused.

However, according to the present disclosure, the distance D by which the transducer 121 moves in a vertical direction by the vertical movement unit 130 is not limited to the above-mentioned distance.

The ultrasonic waves emitted by the transducer 121 may be focused under the skin of a person being treated and generate heat.

According to the present disclosure, since the vertical movement unit 130 may move the transducer 121 in a vertical direction, it may be possible for an operator to adjust the depth at which ultrasonic waves are focused under a person's skin by moving the transducer 121 in a vertical direction with a simple operation without having to replace the cartridge 120 to adjust the focal distance of ultrasonic waves.

The vertical movement unit 130 may move the transducer 121 in a vertical direction by a magnetic force.

Specifically, the vertical movement unit 130 may immediately move the transducer 121 in a vertical direction by a magnetic force to quickly adjust the depth D1 and D2 at which ultrasonic waves are focused. Therefore, according to the present disclosure, it may be possible to minimize focus of ultrasonic waves on subcutaneous points that do not require treatment.

The vertical movement unit 130 may include a magnet 131 and a magnetic body 132.

One of the magnet 131 and the magnetic body 132 may be installed in the housing 110, specifically, inside the second case 112, and the other may be fixed to the transducer 121.

The magnetic body 132 may be located below or above the magnet 131 and may approach the magnet 131 by a magnetic force of the magnet 131.

It may be desirable that the magnetic body 132 be a ferromagnetic body made of iron, cobalt, nickel, or an alloy thereof, but any material that can approach the magnet 131 by the magnetic force of the magnet 131 may be possible.

When the magnet 131 and the magnetic body 132 approach or move away from each other in a vertical direction in the space inside the housing 110, the transducer 121 may also move in a vertical direction.

Hereinafter, for convenience of explanation, an example of the magnet 131 installed in the second case 112 and the magnetic body 132 fixed to the transducer 121 will be described.

The magnetic body 132 may be guided by a guiding portion 133 connected to the magnet 131 to be movable in a vertical direction.

The guiding portion 133 may include a holder 133h and a guider 133g.

The magnetic body 132 may be attached to the holder 133h, and the guider 133g may be fixed to the bottom of the magnet 131.

The holder 133h may slide in a vertical direction inside the guider 133g.

The guider 133g may include a fixing plate g1 fixed to the bottom of the magnet 131 and a guiding plate g2 that protrudes downward from the edge of the fixing plate g1 and guides the movement of the holder 133h.

A stopper 133hs may be formed on the upper side of the holder 133h, and a groove 133gh into which the stopper 133hs is inserted may be formed in the guiding plate g2.

Since the movement of the stopper 133hs may be limited within the inner upper and lower surfaces forming the groove 133gh, the distance at which the holder 133h moves in a vertical direction inside the guider 133g may also be limited to a set distance D.

The magnet 131 may be an electromagnet.

As a current is applied to the magnet 131, an attractive force may act between the magnet 131 and the magnetic body 132. Consequently, the distance between the magnet 131 and the magnetic body 132 may become close.

Meanwhile, the vertical movement unit 130 may further include an elastic unit 134.

The elastic unit 134 may be an elastic body that can separate the magnet 131 and the magnetic body 132 from each other.

When the elastic unit 134 separates the magnet 131 and the magnetic body 132 from each other, as a current is applied to the magnet 131, the amount of the attractive force between the magnet 131 and the magnetic body 132 may be adjusted based on an intensity of the applied current, thereby adjusting the distance between the magnet 131 and the magnetic body 132.

For example, the elastic unit 134 may widen the distance between the magnet 131 and the magnetic body 132 by an elastic restoring force when the intensity of the current applied to the magnet 131 is below a predetermined level.

In addition, when the intensity of the current applied to the magnet 131 is above the predetermined level, the attractive force between the magnet 131 and the magnetic body 132 may narrow the distance between the magnet 131 and the magnetic body 132.

The handpiece 100 for relieving pain and swelling in the skin of a person being treated may further include a controller 140.

The controller 140 may be connected to each of the transducer 121, the vertical movement unit 130, the skin cooling unit 122, and the EMS skin stimulation unit 123.

Specifically, the controller 140 may be connected to each of the transducer 121 and the magnet 131 of the vertical movement unit 130, the thermoelectric element 122t of the skin cooling unit 122 and the EMS control module 123c of the EMS skin stimulation unit 123, so that the controller 140 may transmit a control signal to the magnet 131, the thermoelectric element 122t, and the EMS control module 123c.

Example 1_Control of Skin Cooling Temperature and Skin Irritation

During a treatment using focused ultrasonic waves for a person being treated (e.g., a patient), the temperature of the cooling plate 151 is controlled to 3° C. to 5° C., and the intensity and the frequency of the microcurrent of the EMS pad 123p are controlled to 80 mA to 100 mA and 1 kHz to 10 kHz, respectively.

Comparative Example 1_Skin Cooling Temperature

During a treatment using focused ultrasonic waves for a person being treated (e.g., a patient), the temperature of the cooling plate 122p is controlled to 3° C. to 5° C., and the intensity of the microcurrent of the EMS pad 123p is controlled to 0 mA.

Experimental Example 1_Experiment on Patient's Pain

Twenty female patients in their 40s weighing between 48 kg and 73 kg were the subjects of the experiment, and the subjects were randomly divided into Group A and Group B, each having 10 subjects. In the case of Group A, an increase or decrease in pain was observed while a treatment using focused ultrasonic waves was performed on wrinkles around the right eye of the patients under the conditions of Comparative Example 1 after a treatment using focused ultrasonic waves had been performed on wrinkles around the left eye of the patients under the conditions of Example 1. In the case of Group B, an increase or decrease in pain was observed while a treatment using focused ultrasonic waves was performed on wrinkles around the right eye of the patients under the conditions of Example 1 after a treatment using focused ultrasonic waves had been performed on wrinkles around the left eye of the patients under the conditions of Comparative Example 1.

When the treatment under the conditions of Comparative Example 1 began after the treatment under the conditions of Example 1, all the subjects in Group A felt an increase in pain, and Table 1 below shows how much pain increased in the subjects in Group A.

In Table 1 below, a score of 5 was given when subjects felt a very significant increase in pain, 4 was given when subjects felt a significant increase in pain, 3 was given when subjects felt a moderate increase in pain, 2 was given when subjects felt a slight increase in pain, and 1 was given when subjects did not feel an increase in pain.

TABLE 1

| | Subject | | | | | | | | | |
|---|---|---|---|---|---|---|---|---|---|---|
| | 1 | 2 | 3 | 4 | 5 | 6 | 7 | 8 | 9 | 10 |
| Increase in Pain | 3 | 4 | 3 | 4 | 5 | 4 | 4 | 3 | 3 | 4 |

All the subjects in Group A experienced a significant increase in pain when the treatment under the conditions of Comparative Example 1 began after the treatment under the conditions of Example 1.

All the subjects in Group B felt pain relief when the treatment under the conditions of Example 1 began after the treatment under the conditions of Comparative Example 1. Table 2 below shows how much pain relief the subjects in Group B felt.

In Table 2 below, a score of A was given when subjects felt very great pain relief, B was given when subjects felt great pain relief, C was given when subjects felt moderate pain relief, D was given when subjects felt slight pain relief, and F was given when subjects did not feel pain relief.

TABLE 2

| | Subject | | | | | | | | | |
|---|---|---|---|---|---|---|---|---|---|---|
| | 1 | 2 | 3 | 4 | 5 | 6 | 7 | 8 | 9 | 10 |
| Decrease in Pain | B | B | A | B | A | A | B | A | A | A |

All the subjects in Group B experienced significant pain relief when the treatment under the conditions of Example 1 began after the treatment under the conditions of Comparative Example 1. In other words, it was confirmed that pain in the skin of a person being treated was greatly alleviated when the treatment using focused ultrasonic waves was performed according to Example 1 of the present disclosure.

Experimental Example 2_Experiment on Patient's Swelling

Twenty female patients in their 40s weighing between 48 kg and 73 kg were the subjects of the experiment, and the subjects were randomly divided into Group A and Group B, each having 10 subjects. In the case of Group A, it was observed how much swelling occurred while a treatment using focused ultrasonic waves was performed on wrinkles around the left eye of the patients under the conditions of Example 1 after a treatment using focused ultrasonic waves without skin cooling and an EMS current stimulation had been performed on wrinkles around the right eye of the patients. In the case of Group B, it was observed how much swelling occurred while a treatment using focused ultrasonic waves was performed on wrinkles around the left eye of the patients under the conditions of Comparative Example 1 after a treatment using focused ultrasonic waves without skin cooling and an EMS current stimulation had been performed on wrinkles around the right eye of the patients.

It was visually confirmed that less swelling had occurred around the left eye of all the subjects in Group A than around the right eye.

Table 3 below shows the scores given for swelling around the left eye when a score of 5 was given for swelling around the right eye. When the degree of swelling around the left eye is 100% to 80% of the swelling around the right eye, a score of 5 is given; when the degree of swelling around the left eye is 79% to 60% of the swelling around the right eye, a score of 4 is given; when the degree of swelling around the left eye is 59% to 40% of the swelling around the right eye, a score of 3 is given; when the degree of swelling around the left eye is 39% to 20% of the swelling around the right eye, a score of 2 is given; and when the degree of swelling around the left eye is 19% to 0% of the swelling around the right eye, a score of 1 is given.

TABLE 3

| | Subject | | | | | | | | | |
|---|---|---|---|---|---|---|---|---|---|---|
| | 1 | 2 | 3 | 4 | 5 | 6 | 7 | 8 | 9 | 10 |
| Degree of Swelling | 2 | 2 | 1 | 1 | 1 | 1 | 1 | 2 | 1 | 1 |

It was confirmed that the treatment using focused ultrasonic waves according to Example 1 was highly effective in reducing swelling.

It was also visually confirmed that less swelling had occurred around the left eye of all the subjects in Group B than around the right eye.

Table 4 below shows the scores given for swelling around the left eye when a score of 5 was given for swelling around the right eye. When the degree of swelling around the left eye is 100% to 80% of the swelling around the right eye, a score of 5 is given; when the degree of swelling around the left eye is 79% to 60% of the swelling around the right eye, a score of 4 is given; when the degree of swelling around the left eye is 59% to 40% of the swelling around the right eye, a score of 3 is given; when the degree of swelling around the left eye is 39% to 20% of the swelling around the right eye, a score of 2 is given; and when the degree of swelling around the left eye is 19% to 0% of the swelling around the right eye, a score of 1 is given.

TABLE 4

| | Subject | | | | | | | | | |
|---|---|---|---|---|---|---|---|---|---|---|
| | 1 | 2 | 3 | 4 | 5 | 6 | 7 | 8 | 9 | 10 |
| Degree of Swelling | 2 | 2 | 2 | 3 | 3 | 3 | 4 | 3 | 3 | 2 |

The treatment using focused ultrasonic waves according to Comparative Example 1 was effective in reducing swelling, but was not more effective than the treatment using focused ultrasonic waves according to Example 1.

All components in the embodiments of the present disclosure have been described as being combined or operating in combination, but the present disclosure is not necessarily limited to the embodiments. That is, one or more of the components may be selectively combined to operate within the scope of the purpose of the present disclosure.

In addition, unless defined otherwise, all terms used herein, including technical or scientific terms, have a meaning consistent with the meaning commonly understood by a person having ordinary skills in the technical field to which the present disclosure belongs. Commonly used terms such as terms defined in dictionaries should be interpreted as having meanings consistent with the meanings in the context of the related technology, and should not be construed in an ideal or overly formal sense unless explicitly defined in the present disclosure.

The description above is only an exemplary description of the technology of the present disclosure, and various modifications and changes within the scope of the essential characteristics of the present disclosure will be possible to a person having ordinary skill in the technical field to which the present disclosure belongs. Therefore, the embodiments disclosed in the present disclosure are not intended to limit the technology of the present disclosure, but to explain them, and the scope of the technology of the present disclosure is not limited by the embodiments. The scope of the present disclosure should be determined based on the following claims, and all technologies within the scope equivalent thereto should be deemed to be included in the scope of the present disclosure.

The invention claimed is:

1. A handpiece for relieving pain and swelling in skin of a person being treated, comprising:
   a housing;
   a cartridge having a transducer that emits ultrasonic waves; and
   a vertical movement unit mounted in the housing and configured to move the transducer in a vertical direction by a magnetic force,
   wherein the cartridge includes:
   a skin cooling unit for cooling the skin of the person being treated; and
   an electrical muscle stimulation (EMS) skin stimulation unit positioned adjacent to the skin cooling unit and providing an electrical stimulation to the skin of the person,
   the skin cooling unit includes:
   a cooling plate, wherein an opening through which ultrasonic waves generated by the transducer pass is formed at a lower part of the cooling plate, and the cooling plate is in contact with the skin of the person to absorb heat from the skin of the person; and
   a thermoelectric element for absorbing heat from the cooling plate to cool the cooling plate,
   the EMS skin stimulation unit includes:
   an EMS pad for providing the electrical stimulation for relieving pain in the skin of the person; and
   an EMS control module for controlling the electrical stimulation delivered to the skin of the person by the EMS pad,
   the EMS pad is attached to the cooling plate in a form of a film, or the EMS pad is formed integrally with the cooling plate and,
   the temperature of the cooling plate is controlled to 3° C. to 5° C., and
   the electrical stimulation of the EMS pad is a current with an intensity of 80 mA to 100 mA and a frequency of 1 kHz to 10 kHz.

2. The handpiece of claim 1, wherein the vertical movement unit includes:
   a magnet disposed in the housing; and
   a magnetic body fixed to the transducer, wherein the magnetic body is configured to move the transducer in a vertical direction while a distance between the magnet and the magnetic body is adjusted by the magnetic force.

3. The handpiece of claim 2, wherein the vertical movement unit further includes an elastic unit for separating the magnet and the magnetic body from each other.

4. The handpiece of claim 2, wherein the magnet is an electromagnet.

* * * * *